(12) United States Patent
Mukai et al.

(10) Patent No.: US 11,903,647 B2
(45) Date of Patent: Feb. 20, 2024

(54) GAZE DETECTOR, METHOD FOR CONTROLLING GAZE DETECTOR, METHOD FOR DETECTING CORNEAL REFLECTION IMAGE POSITION, AND STORAGE MEDIUM

(71) Applicant: OMRON Corporation, Kyoto (JP)

(72) Inventors: Hitoshi Mukai, Yokohama (JP); Kazuo Yamamoto, Nara (JP); Masaki Suwa, Tokyo (JP); Koichi Kinoshita, Kyoto (JP)

(73) Assignee: OMRON Corporation, Kyoto (JP)

( * ) Notice: Subject to any disclaimer, the term of this patent is extended or adjusted under 35 U.S.C. 154(b) by 828 days.

(21) Appl. No.: 16/977,475

(22) PCT Filed: Feb. 21, 2019

(86) PCT No.: PCT/JP2019/006510
§ 371 (c)(1),
(2) Date: Sep. 2, 2020

(87) PCT Pub. No.: WO2019/176491
PCT Pub. Date: Sep. 19, 2019

(65) Prior Publication Data
US 2021/0052156 A1 Feb. 25, 2021

(30) Foreign Application Priority Data
Mar. 15, 2018 (JP) .................................. 2018-047460

(51) Int. Cl.
*A61B 3/113* (2006.01)
*A61B 3/11* (2006.01)
(Continued)

(52) U.S. Cl.
CPC ............... *A61B 3/113* (2013.01); *A61B 3/111* (2013.01); *A61B 3/112* (2013.01); *G06T 7/74* (2017.01);
(Continued)

(58) Field of Classification Search
CPC ......... A61B 3/111; A61B 3/112; A61B 3/113; A61B 5/1128; A61B 5/163; G06T 7/136;
(Continued)

(56) References Cited

U.S. PATENT DOCUMENTS

| 2012/0069301 A1 | 3/2012 | Hirata |
| 2014/0043459 A1 | 2/2014 | Tsukizawa et al. |

(Continued)

FOREIGN PATENT DOCUMENTS

| CN | 1119809 | 4/1996 |
| CN | 102149325 | 8/2011 |

(Continued)

OTHER PUBLICATIONS

"Search Report of Europe Counterpart Application", dated Nov. 24, 2021, p. 1-p. 13.

(Continued)

*Primary Examiner* — Jack Dinh
(74) *Attorney, Agent, or Firm* — JCIPRNET

(57) ABSTRACT

The purpose of the present invention is to provide a gaze detector with which it is possible to detect a gaze (start point and gaze direction) by a simple configuration. The gaze detector detects a person's gaze, wherein the gaze detector is provided with a camera unit 10 for imaging the face of the person, a projector unit 20 for projecting a prescribed pattern light to the face of the person, a control unit 30 for controlling the presence of projection of the pattern light by the camera unit 10 and the projector unit 20, and a gaze (Continued)

detection processing unit 40 for detecting a gaze from the image of the face of the person imaged by the camera unit.

15 Claims, 11 Drawing Sheets

(51) Int. Cl.
*G06K 9/00* (2022.01)
*G06K 9/46* (2006.01)
*G06T 7/73* (2017.01)
*G06V 40/16* (2022.01)
*G06V 40/18* (2022.01)

(52) U.S. Cl.
CPC .......... *G06V 40/171* (2022.01); *G06V 40/193* (2022.01); *G06T 2207/30201* (2013.01)

(58) Field of Classification Search
CPC .......... G06T 7/246; G06T 7/521; G06T 7/73; G06T 7/74; G06T 2207/10016; G06T 2207/10048; G06T 2207/30201; G06V 40/171; G06V 40/193; G06K 9/00281; G06K 9/0061; G06K 9/4661
See application file for complete search history.

(56) References Cited

U.S. PATENT DOCUMENTS

2017/0091520 A1 3/2017 Ishii et al.
2017/0196451 A1 7/2017 Tian

FOREIGN PATENT DOCUMENTS

| | | |
|---|---|---|
| CN | 102159136 | 8/2011 |
| CN | 102510734 | 6/2012 |
| CN | 103679180 | 3/2014 |
| CN | 107665040 | 2/2018 |
| JP | H07104170 | 4/1995 |
| JP | 2012115505 | 6/2012 |
| JP | 2013106645 | 6/2013 |
| JP | 2014067102 | 4/2014 |
| JP | 2016110444 | 6/2016 |
| WO | 2018000020 | 1/2018 |

OTHER PUBLICATIONS

"International Search Report (Form PCT/ISA/210) of PCT/JP2019/006510," dated May 28, 2019, with English translation thereof, pp. 1-2.

"Written Opinion of the International Searching Authority (Form PCT/ISA/237) of PCT/JP2019/006510," dated May 28, 2019, with English translation thereof, pp. 1-8.

Robert S. Allison et al., "Combined head and eye tracking system for dynamic testing of the vestibular system," IEEE Transactions on Biomedical Engineering, vol. 43, Nov. 1996, pp. 1073-1082.

Ruian Liu et al., "Single Camera Remote Eye Gaze Tracking Under Natural Head Movements," ICAT 2006: Lecture Notes in Computer Science, vol. 4282, Jan. 2006, pp. 614-623.

Kiyoaki Tokunou et al., "Automated thresholding for real-time image processing in video-based eye-gaze detection," Proceedings of the 20th Annual International Conference of the IEEE Engineering in Medicine and Biology Society, vol. 20, Oct. 1998, pp. 748-751.

"Search Report of Europe Counterpart Application", dated Apr. 12, 2022, p. 1-p. 15.

"Office Action of China Counterpart Application", dated Jul. 28, 2023, with English translation thereof, p. 1-p. 24.

Brightness distribution on a vicinity of a corneal reflex image (horizontal direction)

GAZE DETECTOR, METHOD FOR CONTROLLING GAZE DETECTOR, METHOD FOR DETECTING CORNEAL REFLECTION IMAGE POSITION, AND STORAGE MEDIUM

CROSS-REFERENCE TO RELATED APPLICATION

This application is a 371 application of international application of PCT application serial no. PCT/JP2019/006510, filed on Feb. 21, 2019, which claims the priority benefit of Japan application no. 2018-047460, filed on Mar. 15, 2018. The entirety of each of the above-mentioned patent applications is hereby incorporated by reference herein and made a part of this specification.

BACKGROUND OF THE INVENTION

1. Field of the Invention

The invention relates a gaze detector mounted in a driver monitoring system or disposed in a work site, etc., for example, to be used for gaze detection, a gaze detector capable of vestibulo-ocular reflex (VOR) measurement or face recognition, a method for controlling the gaze detector, a method for detecting a corneal reflection image position, a computer program, and a storage medium.

2. Description of Related Art

In Patent Document 1, a gaze detector that detects a gaze direction by detecting a Purkinje image (a corneal reflection image of the application) has been disclosed.

The gaze detector includes a display unit, a wide-angle camera, an illumination light source, an infrared camera, an input unit, a storage medium access apparatus, a storage unit, and a control unit.

A distance from a camera unit which generates an imaging a user's face to the user's face is estimated. Whether it is changed to a bright pupil state in which the entire pupil of the user's eye becomes brighter due to light from a light source which illuminates the camera unit and the user's eye is determined according to a ratio of the distance from the camera unit to the user's face to an interval between the camera unit and the light source. In the case of determining that it is not changed to the bright pupil state, the corneal reflection image of the light source and the pupil center of the user are detected from the image, and the gaze direction or the gaze position of the user is detected according to the positional relationship between the pupil center and the corneal reflection image.

Problems to be Solved by the Invention

In the gaze detector according to Patent Document 1, in order to detect the gaze direction, a wide-angle camera, an infrared camera, and an illumination light sources are necessary structure components, and two cameras are installed. Therefore, the manufacturing cost of the gaze detector is high, and the gaze detector has a large size.

PRIOR ART DOCUMENT

Patent Document

[Patent Document 1] Japanese Laid-Open No. 2014-67102

SUMMARY OF THE INVENTION

Means for Solving the Problem and its Effect

The invention has been made in view of the above issues and has the objective of providing a gaze detector capable of detecting a gaze (start point and gaze direction) with a simple configuration, a method for controlling the gaze detector, a method for detecting a corneal reflection image position, a computer program, and a storage medium.

In order to achieve the objective, a gaze detector (1) according to the disclosure is a gaze detector that detects a gaze of a person and includes: a camera unit, imaging a face of a person; a projection unit, projecting prescribed pattern light to the face of the person; a control unit, controlling presence of projection of the pattern light by the camera unit and the projection unit; and a gaze detection processing unit, detecting a gaze from the image of the face of the person imaged by the camera unit.

According to the gaze detector (1), by imaging while projecting the pattern light to the face of the person, even with one camera unit (comparable to the camera in the conventional example), imaging for gaze detection can be carried out. If one camera unit can suffice for the configuration of the gaze detector, the manufacturing cost of the apparatus can be reduced, and the apparatus can be miniaturized.

In addition, regarding a gaze detector (2) according to the disclosure, in the gaze detector (1), the gaze detection processing unit includes: a first calculation unit, using an image of the face which is imaged by the camera unit and in which the pattern light is not projected to calculate a pupil center in an eye of the person; a second calculation unit, using an image of the face which is imaged by the camera unit and in which the pattern light is projected to calculate a position of a corneal reflection image in the eye of the person; and a third calculation unit, using the image of the face which is imaged by the camera unit and in which the pattern light is projected to calculate a three-dimensional position vector of a predetermined part of the face.

According to the gaze detector (2), even if there is one camera unit, by using the gaze detection processing unit, the pupil center can be calculated, the position of the corneal reflection image can be calculated, and the three-dimensional position vector of the predetermined part of the face can be calculated. If these calculation results are used, a gaze (start point and gaze direction) can be detected.

In addition, regarding a gaze detector (3) according to the disclosure, the gaze detector (1) or (2) includes: a fourth calculation unit, detecting a change of a pupil center in an eye of the person over time to calculate an eye movement; a fifth calculation unit, detecting a surface shape of the face from a three-dimensional position vector of a predetermined part of the face and calculating a head movement of the person based on a change of an orientation of the face surface shape over time. In addition, the gaze detector uses the eye movement and the head movement to detect vestibulo-ocular reflex (VOR).

VOR induced by the head movement is an involuntary eye movement which reverses the eyeball at a substantially same speed during the head movement and suppresses blurring of the retinal image.

According to the gaze detector (3), with the fourth calculation unit that calculates the eye movement and the fifth calculation unit that calculates the head movement, VOR which is an involuntary eye movement that reverses the eyeball at a substantially same speed during the head movement and suppresses blurring of the retinal image can be calculated.

In addition, regarding a gaze detector (4) according to the disclosure, any one of the gaze detector (1) to (3) includes: a sixth calculation unit, calculating a surface shape of the face of the person from a three-dimensional position vector of a predetermined part of the face of the person. The gaze detector uses the calculated surface shape of the face of the person to perform face recognition.

According to the gaze detector (4), with the sixth calculation part capable of calculating the surface shape of the face of the person, face recognition can be carried out based on the surface shape of the face.

In addition, regarding a gaze detector (5) according to the disclosure, in any one of the gaze detector (1) to (4), a prescribed pattern of the pattern light becomes a binary pattern that differs for each location.

According to the gaze detector (5), the pattern light differs for each location. Since the pattern light is arranged as a binary pattern of black and white, for example, the three-dimensional position vector of each location can be determined easily and detected quickly, and the detection of the gaze, detection of VOR, or face recognition can be carried out in a short time.

In addition, regarding a gaze detector (6) according to the disclosure, in any one of the gaze detector (1) to (5), the projection unit projects the pattern light with light in a predetermined invisible wavelength range, the camera unit is sensitive in the predetermined wavelength range, and the gaze detector further includes an illuminator that emits the light in the predetermined wavelength range.

As the light in the predetermined invisible wavelength range, an example is near infrared light. Near infrared light refers to infrared light with a short wavelength of about 0.7 micrometers to 2.5 micrometers, and used for a lighting apparatus for a night-vision camera, infrared communication, vein authentication, etc.

The wavelength of the near-infrared band is not recognized by the human eye, so near infrared light does not interfere with people. According to the gaze detector (6), the light amount of the near infrared light necessary for imaging is ensured. Even if the light amount of natural light is insufficient, the gaze detection, VOR detection, or face recognition can still be performed at high precision.

In addition, a method (1) for controlling a gaze detector is a method for controlling the gaze detector (1). The method (1) includes: a step of turning on the projection unit and projecting the pattern light to the face of the person; a step of imaging the face on which the pattern light is projected by the camera unit; a step of outputting an image imaged in the step to the gaze detection processing unit; a step of turning off the projection unit; a step of imaging the face on which the pattern light is not projected by the camera unit; and a step of outputting an image imaged in the step to the gaze detection processing unit.

According to the method (1) for controlling the gaze detector, even if there is one camera unit, the corneal reflection image position and the eye three-dimensional position vector can still be calculated from the image imaged in the state in which the projection unit is turned on, while the pupil center can still be detected from the image imaged in the state in which the projection unit is turned off, and imaging for gaze detection can be executed with simple control.

In addition, a method (2) for controlling a gaze detector is a method for controlling the gaze detector (6). The method (2) includes: a step of turning on the projection unit and turning off an illuminator; a step of imaging the face on which the pattern light is projected by the camera unit; a step of outputting an image imaged in the step to the gaze detection processing unit; a step of turning off the projection unit and turning on the illuminator; a step of imaging the face on which the pattern light is not projected by the camera unit; and a step of outputting an image imaged in the step to the gaze detection processing unit.

According to the method (2) for controlling the gaze detector, even if there is one camera unit, the corneal reflection image position and the eye three-dimensional position vector can still calculated from the image imaged by the camera unit in the state in which the projection unit which emits pattern light is turned on and the illuminator which does not emit pattern light is turned off, while the pupil center can still be detected from the image imaged by the camera unit in the state in which the projection unit is turned off and the illuminator is turned on, and imaging for gaze detection can be executed with simple control.

In addition, since the light in the predetermined invisible wavelength band is not recognized by the human eye, the light amount of the illuminator necessary for imaging is ensured, and the gaze detection, VOR detection, or face recognition can still be performed at high precision.

In addition, a method (1) for detecting a corneal reflection image position according to the disclosure is a method for detecting a corneal reflection image position for gaze detection using any one of the gaze detector (1) to (6). The method includes: a step of receiving the imaged image and a pupil center position; a step of setting a search area in a vicinity of the pupil center position; a step of scanning pixels in the search area one after another; a step of determining whether a scanning result becomes a maximum value of brightness; a step of adopting a value of the brightness as the maximum value if it is determined that a dynamic range of brightness is equal to or greater than a threshold; and a step of outputting a position of a pixel which denotes the maximum value and has a shortest distance from the pupil center as the corneal reflection image position.

According to the method (1) for detecting the corneal reflection image position, even if the light amount from the projection unit is low, the detection of the corneal reflection image position for gaze detection can still be reliably performed.

In addition, regarding a method (2) for detecting a corneal reflection image position, in the method (1) for the corneal reflection image position, a difference between the maximum value and a minimum value of brightness is set as the dynamic range.

According to the method (2) for detecting the corneal reflection image position, even if the light amount from the projection unit is low, the corneal reflection image position for gaze detection can still be reliably narrowed down.

In addition, regarding a method (3) for detecting a corneal reflection image position, in the method (1) for detecting the corneal reflection image position, a difference between the maximum value and a median value of brightness is set as the dynamic range.

According to the method (3) for detecting the corneal reflection image position, even if the light amount from the projection unit is low, the detection of the corneal reflection image position for gaze detection can be more resistant to noise.

In addition, regarding a method (4) for detecting a corneal reflection image position, any one of the methods (1) to (3) for detecting the corneal reflection image position includes a step of outputting, in a case where it is determined that there is no maximum value that is adoptable in a brightness distribution, the corneal reflection image position of a prior frame.

According to the method (4) for detecting the corneal reflection image position, even in the case where it is determined that there is no maximum value that is adoptable in the brightness distribution, the output of the corneal reflection image position for gaze detection can still be reliably performed without failure.

In addition, regarding a method (5) for detecting a corneal reflection image position, any one of the methods (1) to (3) for detecting the corneal reflection image position includes a step of outputting, in a case where it is determined that there is no maximum value that is adoptable in a brightness distribution, a current corneal reflection image position predicted from a prior frame.

The prior frame may also be, for example, several prior frames.

According to the method (5) for detecting the corneal reflection image position, even in the case where it is determined that there is no maximum value that is adoptable in the brightness distribution and the person is moving, the output of the corneal reflection image position for gaze detection can still be properly performed.

In addition, regarding a method (6) for detecting a corneal reflection image position, any one of the methods (1) to (3) for detecting the corneal reflection image position includes a step of outputting, in a case where it is determined that there is one maximum value that is adoptable in a brightness distribution, a position of the maximum value as the corneal reflection image position.

According to the method (6) for detecting the corneal reflection image position, the detection process can be simplified, and the load of software processing can be alleviated.

A computer program (1) according to the disclosure is a computer program for causing at least one computer to execute a detection process for a position of a corneal reflection image for gaze detection using any of the gaze detector (1) to (6). The computer program causes the at least one computer to execute: a step of receiving the imaged image and a pupil center position; a step of setting a search area in a vicinity of the pupil center position; a step of scanning pixels in the search area one after another; a step of determining whether a scanning result becomes a maximum value of brightness; a step of adopting a value of the brightness as the maximum value if it is determined that a dynamic range of brightness is equal to or greater than a threshold; and a step of outputting a position of a pixel which denotes the maximum value and has a shortest distance from the pupil center as the corneal reflection image position.

According to the computer program (1), even if the light amount from the projection unit is low, the at least one computer can still reliably execute the detection of the corneal reflection image position for gaze detection.

A computer readable recording medium (1) according to the disclosure is a computer readable recording medium storing a computer program for causing at least one computer to execute a detection process for a position of a corneal reflection image for gaze detection using any one of the gaze detector (1) to (6). The computer readable recording medium stores the computer program that causes the at least one computer to execute: a step of receiving the imaged image and a pupil center position; a step of setting a search area in a vicinity of the pupil center position; a step of scanning pixels in the search area one after another; a step of determining whether a scanning result becomes a maximum value of brightness; a step of adopting a value of the brightness as the maximum value if it is determined that a dynamic range of brightness is equal to or greater than a threshold; and a step of outputting a position of a pixel which denotes the maximum value and has a shortest distance from the pupil center as the corneal reflection image position.

According to the computer readable recording medium (1), by causing the at least one computer to read the program and execute the respective steps, even if the light amount from the projection unit is low, the at least one computer can still reliably execute the detection of the corneal reflection image position for gaze detection.

DESCRIPTION OF THE EMBODIMENTS

In the following, embodiments of a gaze detector of the invention mounted in a driver monitoring system or disposed in a work site to be used for gaze (start point and gaze direction) measurement, a gaze detector capable of vestibulo-ocular reflex (VOR) measurement or face recognition, a method for controlling the gaze detector, a method for detecting corneal reflection image position, a computer program, and a storage medium will be described based on the drawings.

Application Example

The invention, for example, is suitable for a gaze detector. In the conventional gaze detector, in order to detect the gaze direction, a wide-angle camera, an infrared camera, and an illumination light source are necessary structure components, and two cameras are installed. Therefore, the manufacturing cost of the gaze detector is high, and the gaze detector has a large size.

In the gaze detector according to the invention, by imaging while projecting pattern light to a face of a person, even with one camera unit (comparable to the camera in the conventional example), imaging for gaze detection can be carried out, and a gaze (start point and gaze direction) can be detected by a simple configuration.

Figure 1:
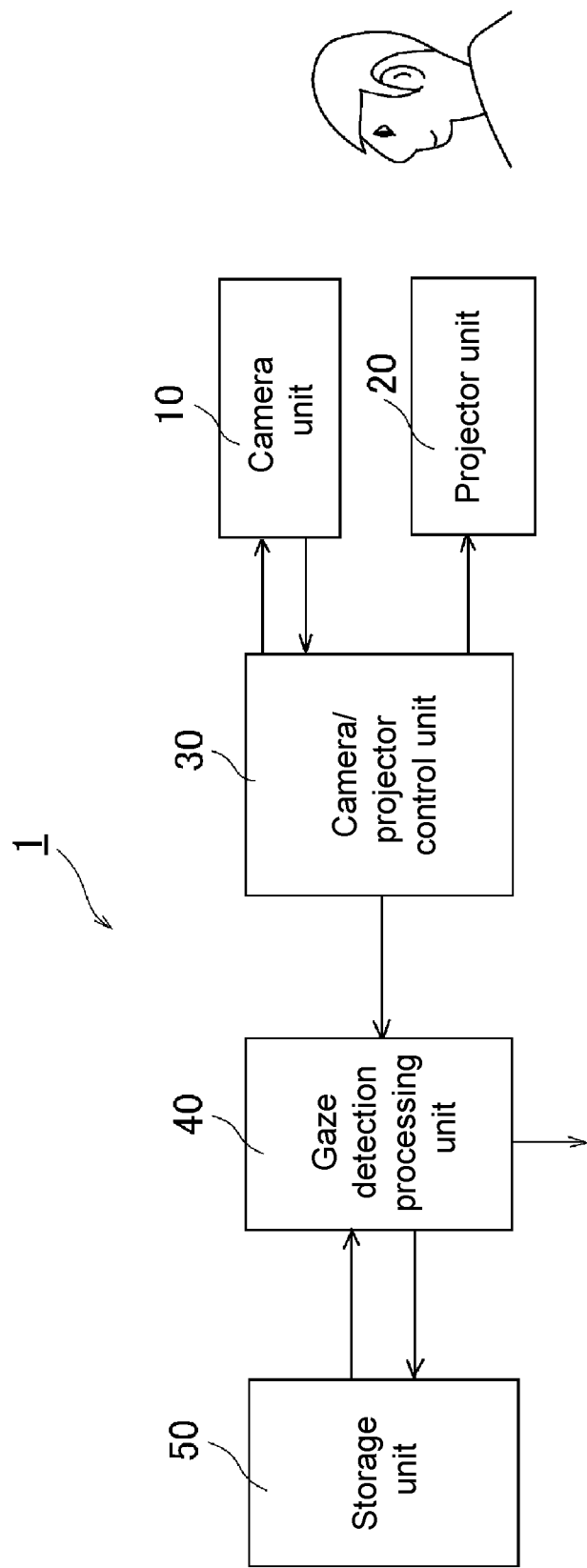
FIG. 1 is a block diagram illustrating a functional configuration of an example of a gaze detector according to an embodiment.

FIG. 1 is a block diagram illustrating a functional configuration of an example of a gaze detector according to an embodiment.

A gaze detector 1, for example, is built and provided in a driver monitoring system (not shown) for monitoring the driving operation of a driver of a vehicle, and is mounted on a vehicle-mounted apparatus side in the driver monitoring system.

The vehicle-mounted apparatus is provided with an inertial sensor that detects an inertial force of the vehicle, a global positioning system (GPS) receiver as a position detection unit, a speaker as a sound output unit, etc. In addition, a communication unit, an external interface (external I/F), etc., are also commonly provided.

In the inertial sensor, an angular velocity sensor that detects an angular velocity of the vehicle is included. Regarding the angular velocity sensor, a sensor at least capable of detecting an angular velocity corresponding to rotation around the vertical axis (yaw direction), that is, angular velocity data corresponding to rotation (turning) of the vehicle toward the left-right direction, such as a gyro sensor (also referred to as a yaw rate sensor), is adopted.

Moreover, regarding the angular velocity sensor, in addition to the one-axis gyro sensor for rotation around the vertical axis, a two-axis gyro sensor that also detects an angular velocity of rotation about the horizontal axis (pitch direction) of the left-right direction, and a three-axis gyro sensor that also detects an angular velocity of rotation about the horizontal axis (roll direction) in the front-rear direction may also be adopted. The gyro sensors may be a vibration gyro sensor, or an optical gyro sensor, a mechanical gyro sensor, etc.

In addition, the inertial sensor may also be configured as including an acceleration sensor that detects the acceleration of the vehicle. The angular sensor and the acceleration sensor may also be mounted in a package. Regarding the acceleration sensor, while a three-axis acceleration sensor that detects the accelerations in three directions, i.e., X-axis, Y-axis, and Z-axis, is commonly adopted, a two-axis or one-axis acceleration sensor may also be adopted.

The GPS receiver receives a GPS signal from a satellite via an antenna at a predetermined interval and detects current location information (latitude, longitude, altitude). The location information detected by the GPS receiver is associated with a location detection time and stored in a location information storage unit. An apparatus for detecting a vehicle location of the vehicle is not limited to the GPS receiver, but may also be a location detection apparatus corresponding to other satellite positioning systems, such as Quasi-Zenith Satellite System of Japan, GLONASS of Russia, Compass of China, etc.

The communication unit is configured to include a communication module for performing data output to a server apparatus via a communication network.

The external interface, for example, is configured as including an interface circuit, a connection connector, etc., for transmitting and receiving data, signals with a vehicle-external device (not shown) such as a vehicle-external camera that images the outside of the vehicle.

The vehicle in which the vehicle-mounted apparatus is mounted is not particularly limited. In the application example, vehicles managed by business operators running various businesses may be the target. For example, a truck managed by a transportation business operator, a bus managed by a bus operator, a taxi managed by a taxi operator, a car-sharing vehicle managed by a car-sharing operator, a rental car managed by a rental car operator, etc., may be the target.

The vehicle-mounted apparatus, for example, may be connected with a server apparatus to be able to communicate via a communication network. The communication network includes a wireless communication network such as a mobile phone network (3G/4G) including a base station or a wireless local area network (LAN), etc., and may include a wired communication network such as a public telephone network, the Internet, or a dedicated network, etc.

In addition, a terminal apparatus (referred to as a business operator terminal in the following) of a business operator that manages a vehicle may be connected with a server apparatus to be able to communicate via a communication network. The business operator terminal may also be a personal computer having a communication function, and may also be a mobile information terminal such as a mobile phone, a smart phone, or a tablet terminal, etc.

The server apparatus accumulates information (referred to as "orientation information" in the following) such as the orientation of the face and/or gaze of the driver of the vehicle obtained by the vehicle-mounted apparatus, and performs a process for evaluating a safety check operation of the driver. The server apparatus, for example, performs a process for respectively evaluating the safety check operations of the driver between a predetermined time before an intersection entry time and a predetermined time after the intersection entry time, and stores the evaluation results.

Then, in the case where there is a request from the business operator terminal, the server apparatus perform a process for providing information such as the evaluation results of the safety check operations of the driver of the vehicle to the operator terminal via the communication network.

Configuration Example

The gaze detector 1 according to the embodiment, as shown in FIG. 1, is configured as including a camera unit 10, a projector unit 20 that emits pattern light, a camera/projector control unit 30 that controls the camera unit 10 and the projector unit 20, a gaze detection processing unit 40 that executes a gaze detection process, and a storage unit 50, for example, The face of the driver is imaged by the camera unit 10, the image of the face that is imaged is processed by the gaze detection processing unit 40, and a gaze is detected. While not shown in the drawings, in addition to gaze detection, the gaze detector 1 according to the embodiment can also detect the eye movement and the head movement of the driver to calculate VOR and can calculate the three-dimensional shape of the face at high precision to perform face recognition.

The camera unit 10, for example, is configured as including, for example, a lens unit, an imaging element unit, an interface unit, a control unit that controls the respective units, which are not shown in the drawings. The imaging element unit is configured as including, for example, an imaging element such as a charge coupled device (CCD), a complementary metal oxide semiconductor (CMOS), etc., a filter, a micro lens, etc. In addition to one that receives visible light to be able to form an image, the imaging element unit may also be an infrared sensor such as a CCD, CMOS or a photodiode, etc., that receives ultraviolet or infrared light to be able to form an image. The camera unit 10 is configured as a single lens camera.

The camera unit 10 images at a predetermined frame rate (e.g., 30 to 60 frames per second), the data of the images imaged by the camera unit 10 are output to the gaze detection processing unit 40 via the camera/projector control unit 30.

The projector unit 20 includes a light emitting element, such as a light emitting diode (LED), and may also be configured as including an infrared LED, etc., so as to be able to image the state of the driver regardless of day or night.

In addition, the projector unit 20 is configured as including a pattern light emitting unit (not shown) so as to be able to emit pattern light to the surface of the face of the driver. The pattern light emitting unit is controlled by a control signal from the camera/projector control unit 30. Here, the pattern light from the pattern light emitting unit is not particularly limited. Any pattern light may be used as long as it is suitable for distance measurement. As excellent pattern light particularly suitable for distance measurement, an example is the pattern light recited in Japanese Patent Application No. 2016-202682, which is a prior application of the applicant. The pattern light of Japanese Patent Application No. 2016-202682 becomes a binary pattern of black and white that differs for each location.

The camera/projector control unit 30, for example, is configured as including a central processing unit (CPU), a memory, etc., and reads a predetermined program stored in the memory, for example, to be interpreted and executed by the CPU, thereby realizing operations described in the following. The camera/projector control unit 30 performs control to control the imaging element unit, the projector unit 20 to emit pattern light (e.g., near infrared light, etc.) from the projector unit 20 and image the reflected light of the pattern light by the imaging element unit, etc.

The gaze detection processing unit 40, for example, is configured as including a CPU, a memory, etc., and reads a predetermined program stored in the memory, for example, to interpret and execute the program by the CPU, thereby realizing operations described in the following. The gaze detection processing unit 40 performs a process for using the image data imaged by the camera unit 10 to perform a gaze detection process and outputting the gaze detection result of each frame to the control unit on the vehicle-mounted apparatus side in the driver monitoring system and outputting to the storage unit 50 to be stored. In addition, the gaze detection processing unit 40 performs a process for reading the corneal reflection image position, etc., in the prior frame that is stored in the storage unit 50, performing a gaze detection process based on the read corneal reflection image position as necessary, and outputting the gaze detection result to the control unit on the vehicle-mounted apparatus side in the driver monitoring system.

The storage unit 50 is configured as one or more memory apparatuses such as a random access memory (RAM), a read-only memory (ROM), a flash memory, a solid state drive (SSD), a hard disk drive (HDD), etc., for example. In addition, the storage unit 50 may also be configured as including a detachable storage apparatus, such as a memory card, etc. The camera/projector control unit 30 may also be configured as including a RAM and a ROM.

Figure 2:
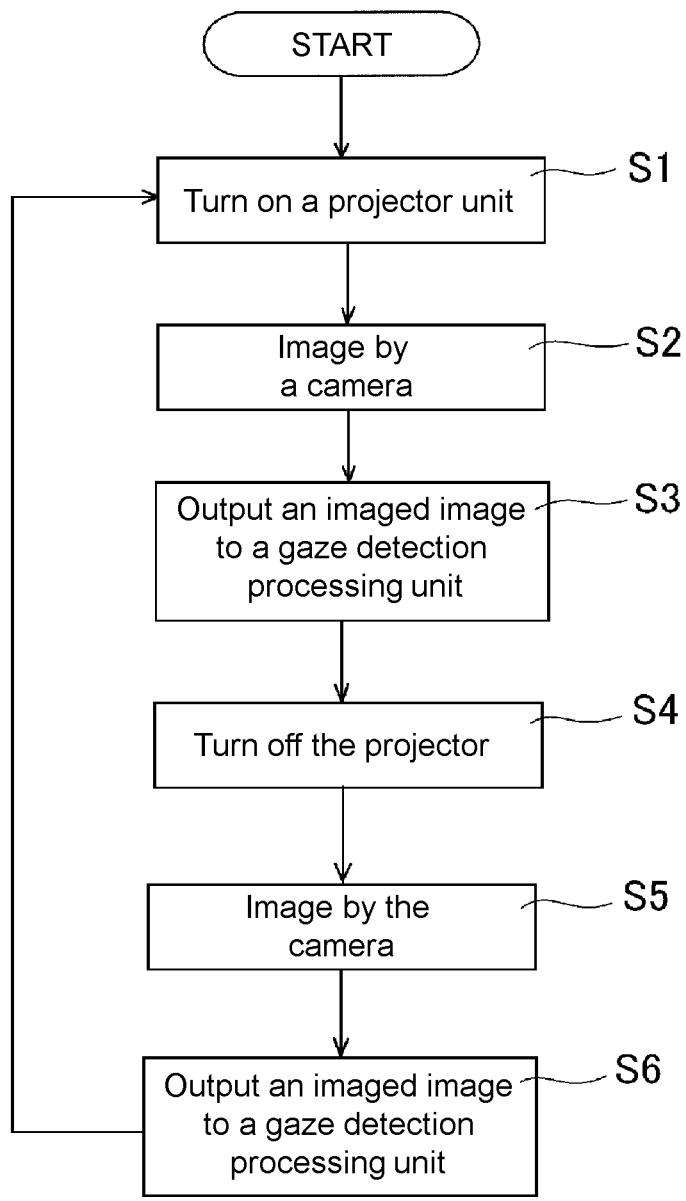
FIG. 2 is a flowchart illustrating processing operations performed by a camera/projector control unit in an example of a gaze detector according to an embodiment.

FIG. 2 is a flowchart illustrating control for imaging by the camera unit 10 and turning on/off the projector 20 in the camera/projector control unit 30 according to an embodiment. The control operation is, for example, executed at a timing at which imaging is executed by the camera unit 10.

Firstly, in Step S1, the projector unit 20 is turned on, and the pattern light is emitted to the face of the driver. Then, in Step S2, the camera unit 10 images the face of the driver on which the pattern light is emitted for detecting the corneal reflection image position and calculating the eye three-dimensional position vector.

Afterwards, in Step S3, the image imaged by the camera unit 10 is output to the gaze detection processing unit 40. Then, in Step S4, the projector unit 20 is turned off. Then, in Step S5, the camera unit 10 images the face of the driver on which the pattern light is not emitted to detect the pupil center.

Afterwards, in Step S6, the image imaged by the camera unit 10 is output to the gaze detection processing unit 40. Then, the flow returns to Step S1. The steps are repetitively executed at a predetermined timing.

Modified Configuration Example

Figure 3:
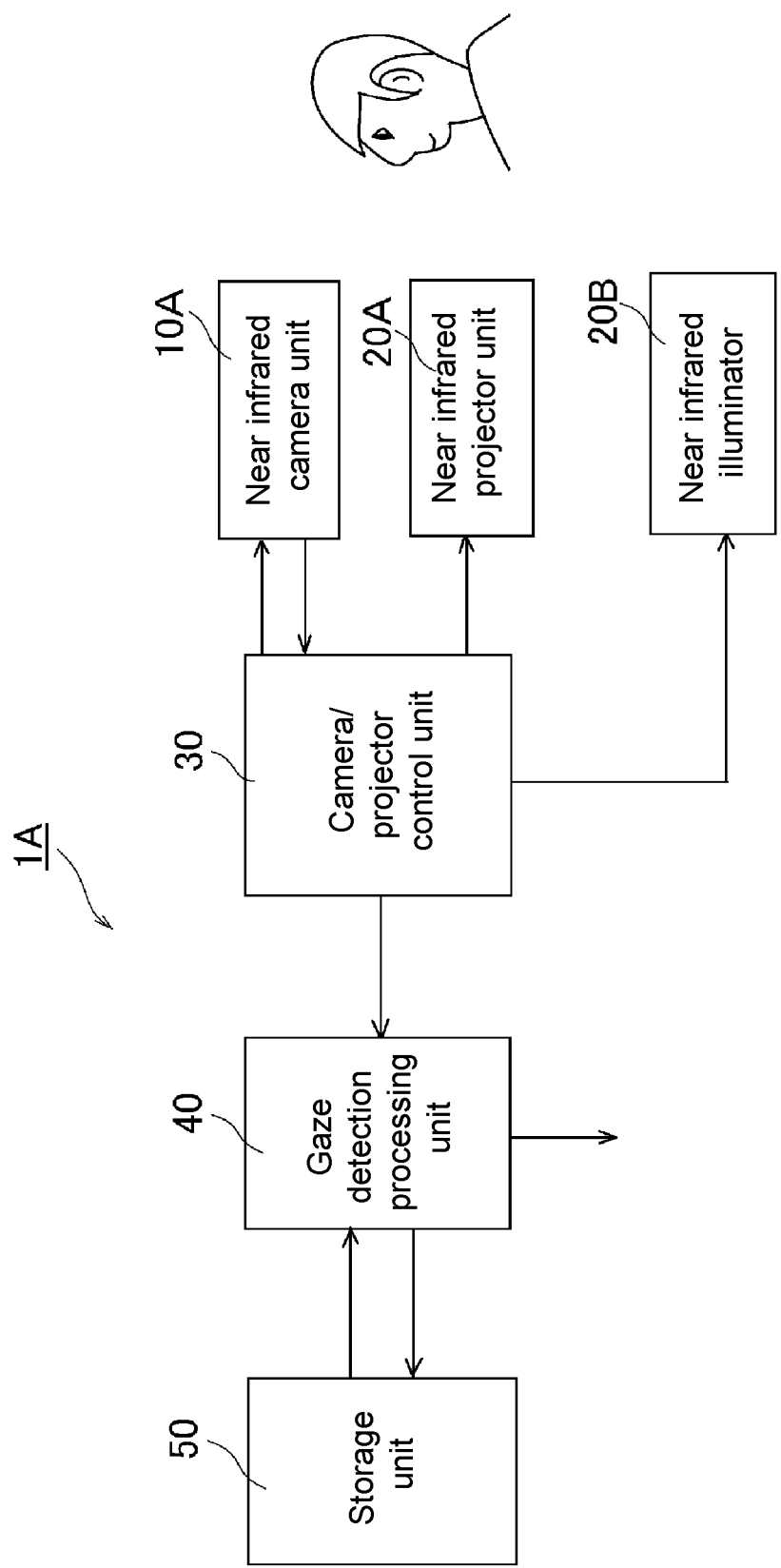
FIG. 3 is a block diagram illustrating a functional configuration of a modified configuration example of a gaze detector according to an embodiment.

In a gaze detector 1A according to the modified configuration example, as shown in FIG. 3, for example, a near infrared camera unit 10A is adopted in place of the camera unit 10 in the gaze detector 1, and a near infrared projector unit 20A is adopted in place of the projector unit 20 that emits the pattern light. In addition, the gaze detector 1A includes a near infrared illuminator 20B capable of detecting the pupil. The remaining camera/projector control unit 30, gaze detection processing unit 40 that executes the gaze detection process, and the storage unit 50 have the same configurations as those of the gaze detector 1 shown in FIG. 1.

The driver is imaged by the camera unit 10A, the image that is imaged is processed by the gaze detection processing unit 40, and the gaze is detected. In addition to gaze detection, the gaze detector 1A according to the modified embodiment as well can detect the eye movement and the head movement of the driver to calculate VOR and calculate the three-dimensional shape of the face at high precision to perform face recognition.

The near infrared camera unit 10A also images at a predetermined frame rate (e.g., 30 to 60 frames per second), the data of the images imaged by the near infrared camera unit 10A are output to the gaze detection processing unit 40 via the camera/projector control unit 30.

The near infrared camera unit 10A, for example, is configured as including a lens unit, an imaging element unit, an interface unit, a control unit that controls the respective units, which are not shown in the drawings, for example. The imaging element unit is configured as including, for example, an imaging element such as a charge coupled device (CCD), a complementary metal oxide semiconductor (CMOS), etc., a filter, a micro lens, etc. The imaging element unit may be a near infrared sensor such a CCD, a CMOS, or a photodiode, etc., that receives infrared light to be able to form an image. The near infrared camera unit 10A may be a single lens camera, and may also be a stereo camera.

The near infrared projector unit 20A is configured as including a light emitting element such as a light emitting diode (LED).

In addition, the near infrared projector unit 20 is configured as including a pattern light emitting unit (not shown) so as to be able to emit pattern light to the surface of the face of the driver. The pattern light emitting unit is controlled by a control signal from the camera/projector control unit 30.

Here, the pattern light from the pattern light emitting unit is not particularly limited, either. Any pattern light may be used as long as it is suitable for distance measurement. As excellent pattern light particularly suitable for distance measurement, an example is the pattern light recited in Japanese Patent Application No. 2016-202682, which is a prior application previously filed by the applicant.

The camera/projector control unit 30, for example, is configured as including a CPU, a memory, an image processing circuit, etc., and reads a predetermined program stored in the memory, for example, to interpret and execute the program by the CPU, thereby realizing operations described in the following. The camera/projector control unit 30 performs control to control the imaging element unit, the near infrared projector unit 20A to emit near infrared pattern light from the near infrared projector unit 20A and image the reflected light of the pattern light by the imaging element unit, etc. The near infrared camera unit 10A images at a predetermined frame rate (e.g., 30 to 60 frames per second), the data of the images imaged by the near infrared camera unit 10A are output to the gaze detection processing unit 40 via the camera/projector control unit 30.

The gaze detection processing unit 40 performs a process for using the image data imaged by the near infrared camera unit 10A to perform a gaze detection process to be described in the following and outputting the gaze detection result of each frame to the control unit on the vehicle-mounted apparatus side in the driver monitoring system and outputting to the storage unit 50 to be stored. In addition, the gaze detection processing unit 40 performs a process for reading the corneal reflection image position, etc., in the prior frame that is stored in the storage unit 50, performs a gaze detection process based on the read corneal reflection image position as necessary and outputting the gaze detection result to the control unit on the vehicle-mounted apparatus side in the driver monitoring system.

Figure 4:
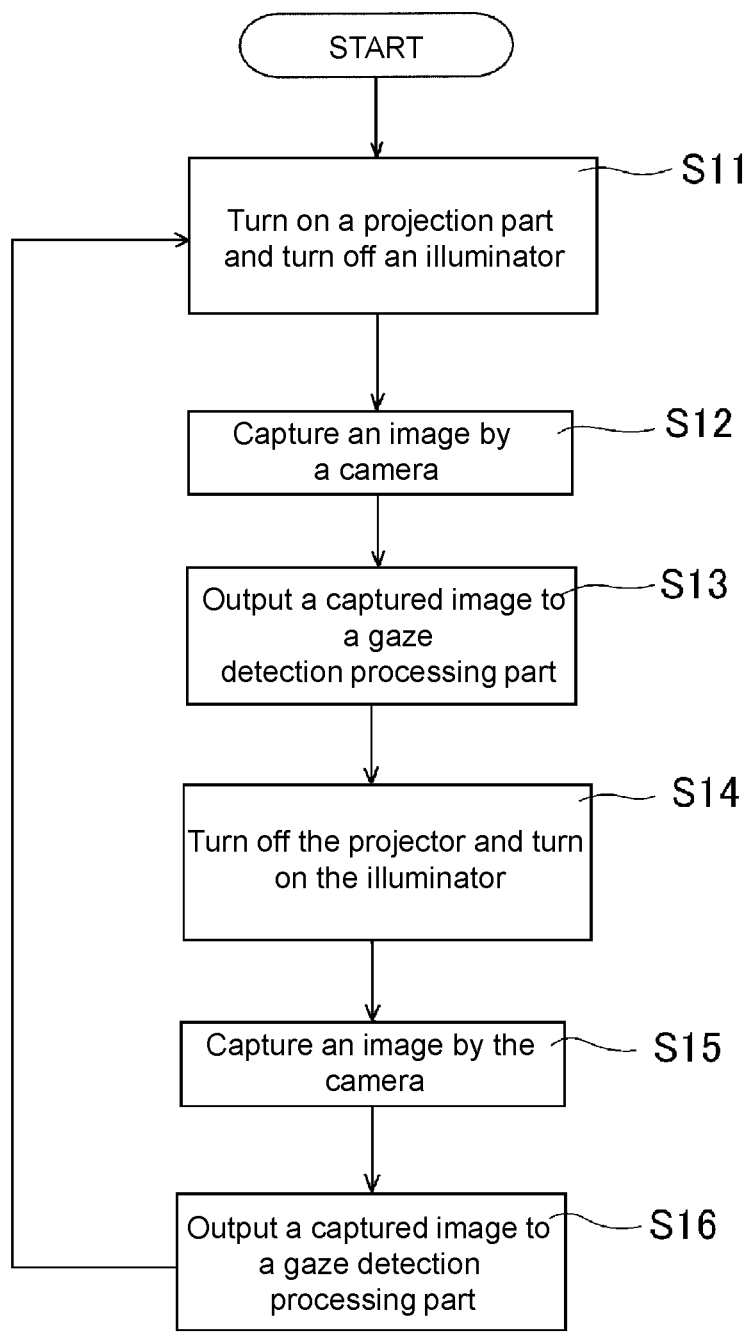
FIG. 4 is a flowchart illustrating processing operations performed by a camera/projector control unit in a modified configuration example of a gaze detector according to an embodiment.

FIG. 4 is a flowchart illustrating control for imaging by the near infrared camera unit 10A and turning on/off the near infrared projector unit 20A and the near infrared illuminator 20B in the camera/projector control unit 30 according to an modified configuration example. The control operation is, for example, executed at a timing at which imaging is executed by the near infrared camera unit 10A.

Firstly, in Step S11, the near infrared projector unit 20A is turned on, and the pattern light is emitted to the face of the driver, while the near infrared illuminator 20B for pupil detection is turned off. Then, in Step S12, the near infrared camera unit 10A images the face of the driver on which the pattern light is emitted for detecting the corneal reflection image position and calculating the eye three-dimensional position vector.

Afterwards, in Step S13, the image imaged by the near infrared camera unit 10A is output to the gaze detection processing unit 40. Then, in Step S14, the near infrared projector unit 20A is turned off, while the near infrared illuminator 20B for detecting the pupil center is turned on.

Next, in Step S15, the near infrared camera unit 10A images the face of the driver on which the pattern light is not emitted to detect the pupil center.

Next, in Step S16, the image imaged by the near infrared camera unit 10A is output to the gaze detection processing unit 40. Then, the flow returns to Step S11. The steps are repetitively executed at a predetermined timing.

Configuration Example of Gaze Detection Processing Unit

Figure 5:
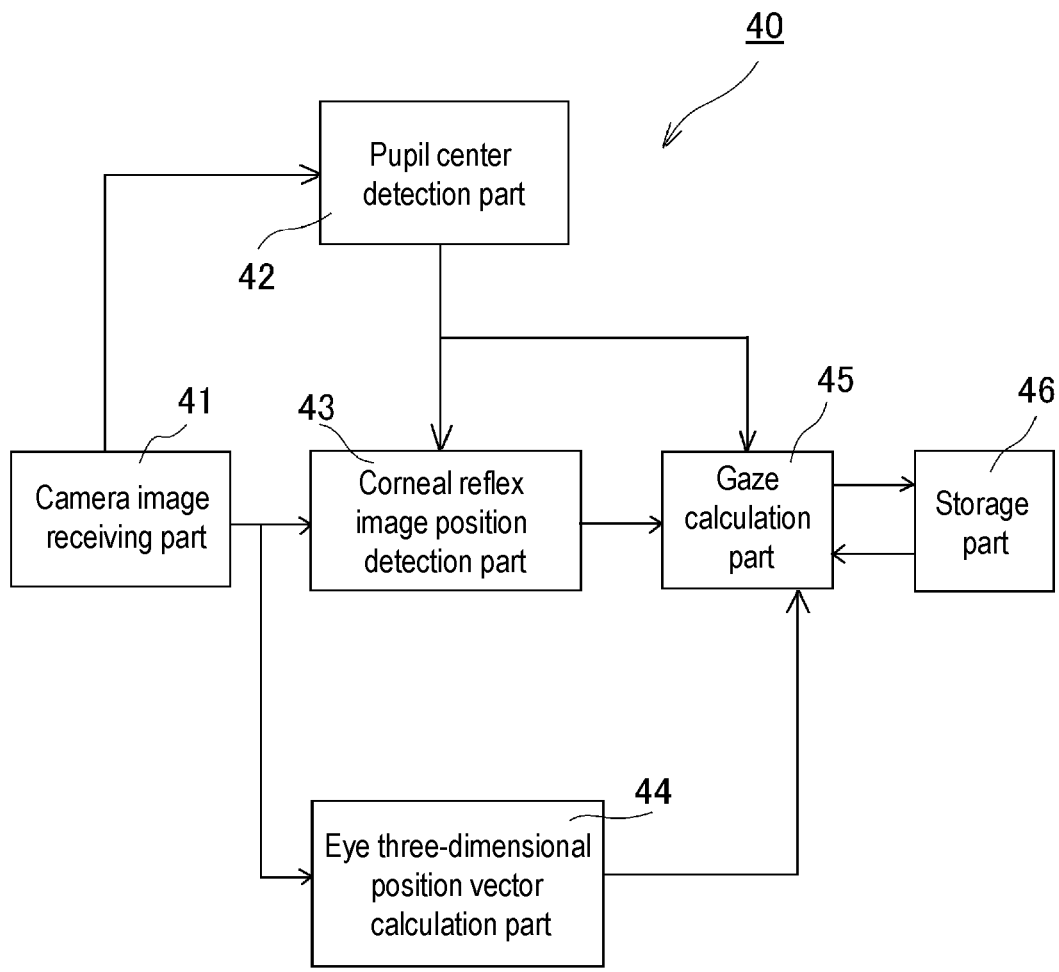
FIG. 5 is a block diagram illustrating an example of a functional configuration of a gaze detection processing unit in a gaze detector according to an embodiment.

FIG. 5 is a block diagram illustrating a functional configuration of the gaze detection processing unit 40 in FIG. 1 and FIG. 3 according to an embodiment. The gaze detection processing unit 40 is configured as including a camera image receiving unit 41, a pupil center detection unit 42, a corneal reflection image position detection unit 43, an eye three-dimensional position vector calculation unit 44, a gaze calculation unit 45, and a storage unit 46.

When receiving the images that are imaged, the camera image receiving unit 41 transmits the image imaged when the projector unit 20 is turned off to the pupil center detection unit 42, while transmitting the image imaged when the projector unit is turned on to the corneal reflection image position detection unit 43 and the eye three-dimensional position vector calculation unit 44.

In the pupil center detection unit 42, the pupil center is detected based on the received imaged image, and a first coordinate value denoting the position of the detected pupil center is transmitted to the corneal reflection image position detection unit 43 and the gaze calculation unit 45.

In the corneal reflection image position detection unit 43, the corneal reflection image is detected based on the received imaged image, and a second coordinate value denoting the position of the detected corneal reflection image is transmitted to the gaze calculation unit 45.

In the eye three-dimensional position vector calculation unit 44, the eye three-dimensional position vector is calculated based on the received imaged image, and the calculated eye three-dimensional position vector is transmitted to the gaze calculation unit 45.

In the gaze calculation unit 45, a gaze (gaze start point and gaze direction) is calculated based on the pupil center coordinate value, the coordinate value of the corneal reflection image, and the eye three-dimensional position vector that have been transmitted, and the gaze is output to the control unit on the vehicle-mounted apparatus side in the driver monitoring system, while a process for transmitting and storing the coordinate value of the corneal reflection image of the current frame in the storage unit 46 and calling the coordinate value of the corneal reflection image of the prior frame from the storage unit 46 is performed.

Figure 6:
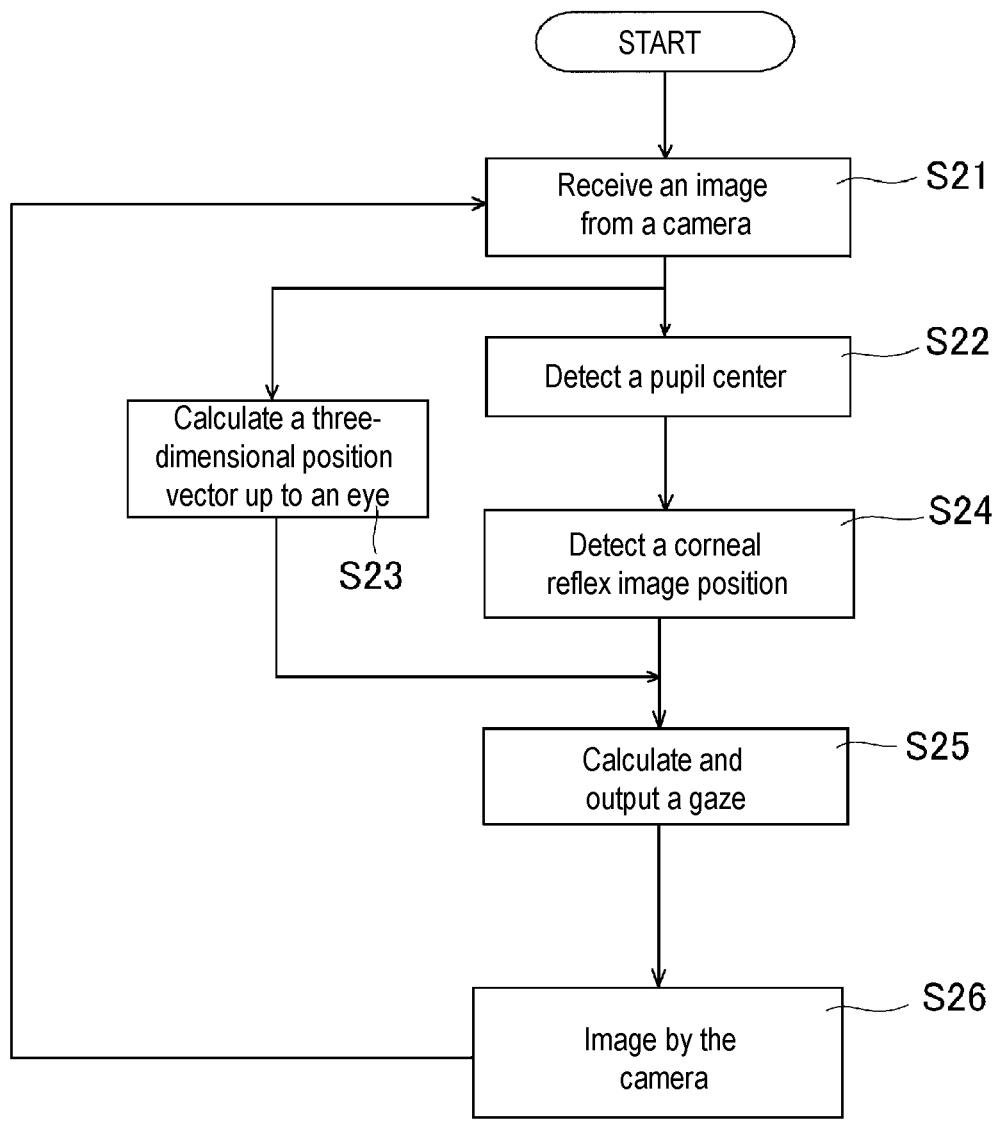
FIG. 6 is a schematic flowchart illustrating processing operations performed by a gaze detection processing unit in a gaze detector according to an embodiment.

FIG. 6 is a flowchart illustrating gaze detection processing operations in the gaze detection processing unit 40 according to Configuration Example 3.

The processing operations are, for example, executed at a timing at which imaging is executed by the camera unit 10 and the imaged images are received.

Firstly, in Step S21, the camera image receiving unit 41 receives the imaged images of the camera unit 10. Next, in Step S22, the pupil center detection unit 42 detects the pupil center from the profile of the pupil based on the received imaged images.

In Step S23, based on the imaged image in which the pattern light is emitted, the eye three-dimensional position vector calculation unit 44 calculates a three-dimensional position vector up to the eye. In Step S24, based on the pupil center detected in Step S22 and the imaged image in which the pattern light is emitted, the corneal reflection image position detection unit 43 detects the corneal reflection image position.

Next, in Step S25, based on the pupil center detected in Step S22, the corneal reflection image position detected in Step S24, and the eye three-dimensional position vector calculated in Step S23, the gaze calculation unit 45 calculates the gaze (gaze start point, gaze direction) and determines the gaze, and outputs the gaze to the control unit on the vehicle-mounted apparatus side in the driver monitoring system.

In addition, in Step S26, after performing the process for writing the detected position of the corneal reflection image to the storage unit 46, the flow returns to Step S21, and the steps are repetitively executed at the predetermined timing.

Figure 7A:
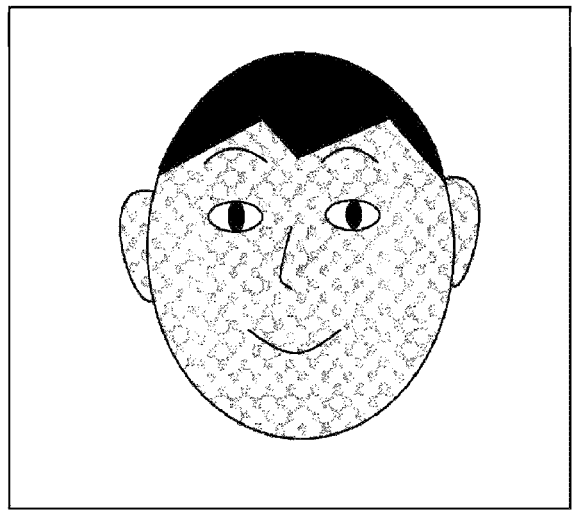
FIGS. 7a and 7b are schematic oblique views for explaining a method for calculating an eye three-dimensional position vector performed by a gaze detection processing unit in a gaze detector according to an embodiment.
Figure 7B:
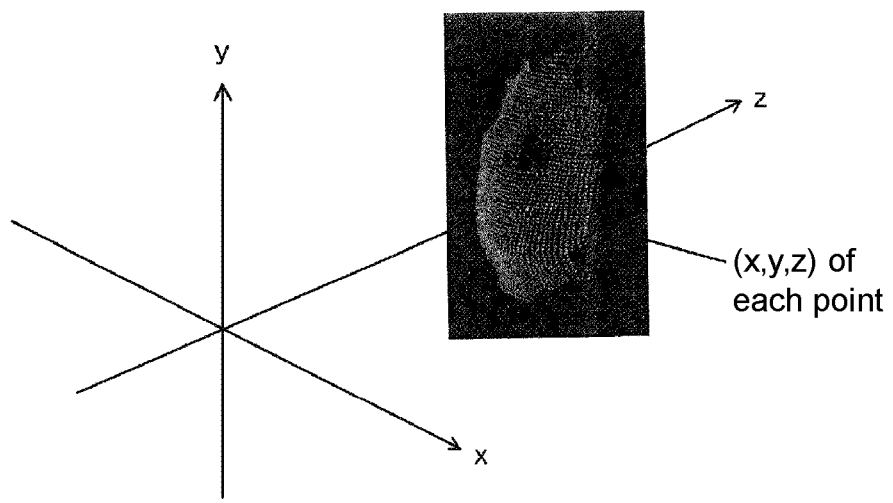

FIGS. 7a and 7b are schematic oblique views for explaining a method for calculating an eye three-dimensional position vector performed by the gaze detection processing unit 40 in the gaze detector according to an embodiment.

FIG. 7a illustrates the state in which the pattern light is emitted to the face of a person.

When the pattern light is emitted, in the eye three-dimensional position vector calculation unit 44, the three-dimensional position vector from the camera is calculated based on the received imaged image, and a graph with a three-dimensional face shape as shown in FIG. 7b is formed from the calculated three-dimensional position vector.

Figure 8A:
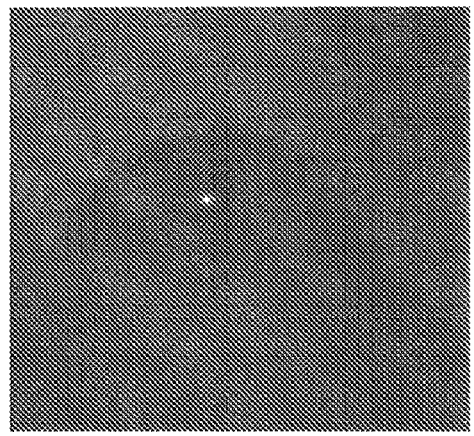
FIGS. 8a and 8b are schematic views for explaining a conventional method for detecting a corneal reflection image.
Figure 8B:
Figure 8B:
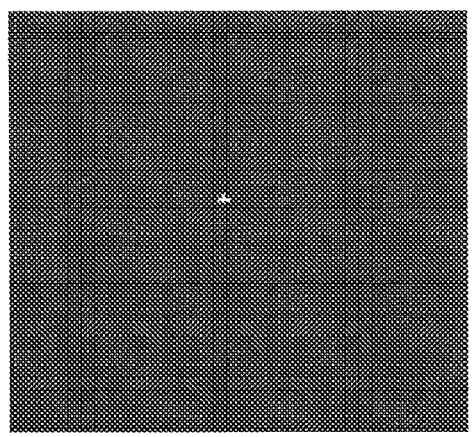

FIGS. 8a and 8b are views for explaining a conventional method for detecting a corneal reflection image. FIG. 8a illustrates a state in which the corneal reflection image is formed in the vicinity of the pupil through illumination by the illuminator. The brightness of such a corneal reflection image is extremely higher than that of the surrounding area. Accordingly, a method including performing an image process on the vicinity of the pupil, extracting a set of pixels with high brightness in the vicinity of the pupil, and determining the position of the center of gravity thereof as the corneal reflection image position FIG. 8b) is used.

Figure 9A:
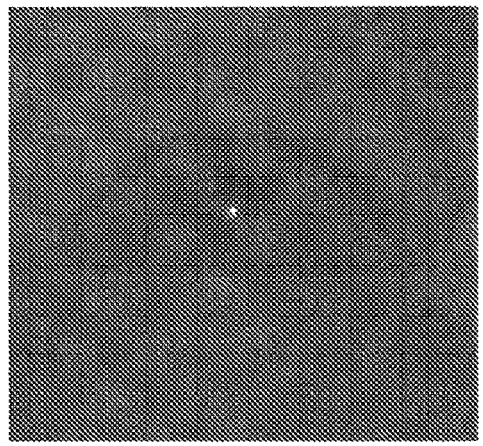
FIGS. 9a and 9b are schematic views illustrating a pattern light projection condition for explaining a corneal reflection image detection process performed by a gaze detection processing unit in a gaze detector according to an embodiment.
Figure 9B:
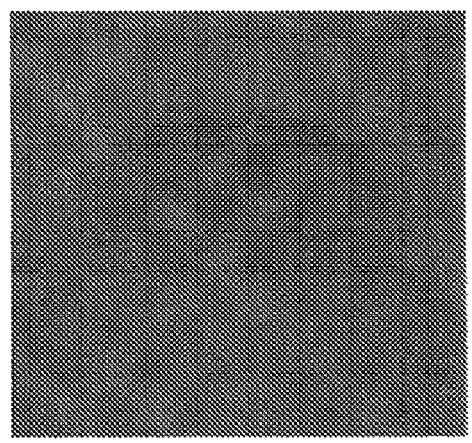

FIGS. 9a and 9b are schematic views illustrating a pattern light projection condition for explaining a corneal reflection image detection process performed by a gaze detection processing unit in a gaze detector according to an embodiment.

FIG. 9a illustrates a state of a case in which the corneal reflection image is in the white region of the pattern light, and FIG. 9b illustrates a state of a case in which the corneal reflection image is in the black region of the pattern light.

When the black region of the pattern light is overlapped with the corneal reflection image position, the brightness of the corneal reflection image is lowered. Therefore, the conventional method assuming that the corneal reflection image has high brightness is not suitable for the embodiment.

Figure 10:
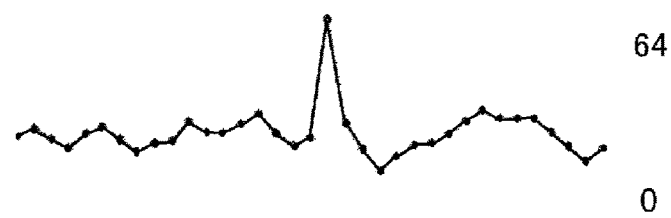
FIG. 10 is a graph illustrating a brightness distribution (in the horizontal direction) on the vicinity of a corneal reflection image in a case where a black region of pattern light is overlapped with a corneal reflection image position in a process performed by a gaze detection processing unit in a gaze detector according to an embodiment.

FIG. 10 is a graph illustrating a brightness distribution (in the horizontal direction) in the vicinity of the corneal reflection image in the case in which the black region of the pattern light is overlapped with the corneal reflection image position, as shown in FIG. 9b. As it can be said that when the black region of the pattern light is overlapped with the corneal reflection image, the brightness of the corneal reflection image is lowered, it is known that, in the corneal reflection image position, a peak steep to a certain extent is present, and the brightness value is changed to the maximum.

Figure 11A:
FIGS. 11a, 11b, and 11c are graphs illustrating brightness distributions (in the horizontal direction) on the vicinity slightly offset in a vertical direction and including a corneal reflection image in a case where a black region of pattern light is overlapped with a corneal reflection image position in a process performed by a gaze detection processing unit in a gaze detector according to an embodiment.
Figure 11B:
Figure 11C:

FIGS. 11a to 11c are graphs illustrating brightness distributions (in the horizontal direction) in the vicinity slightly offset in a vertical direction and including the corneal reflection image in the case where the black region of the pattern light is overlapped with the corneal reflection image position.

Figure 12:
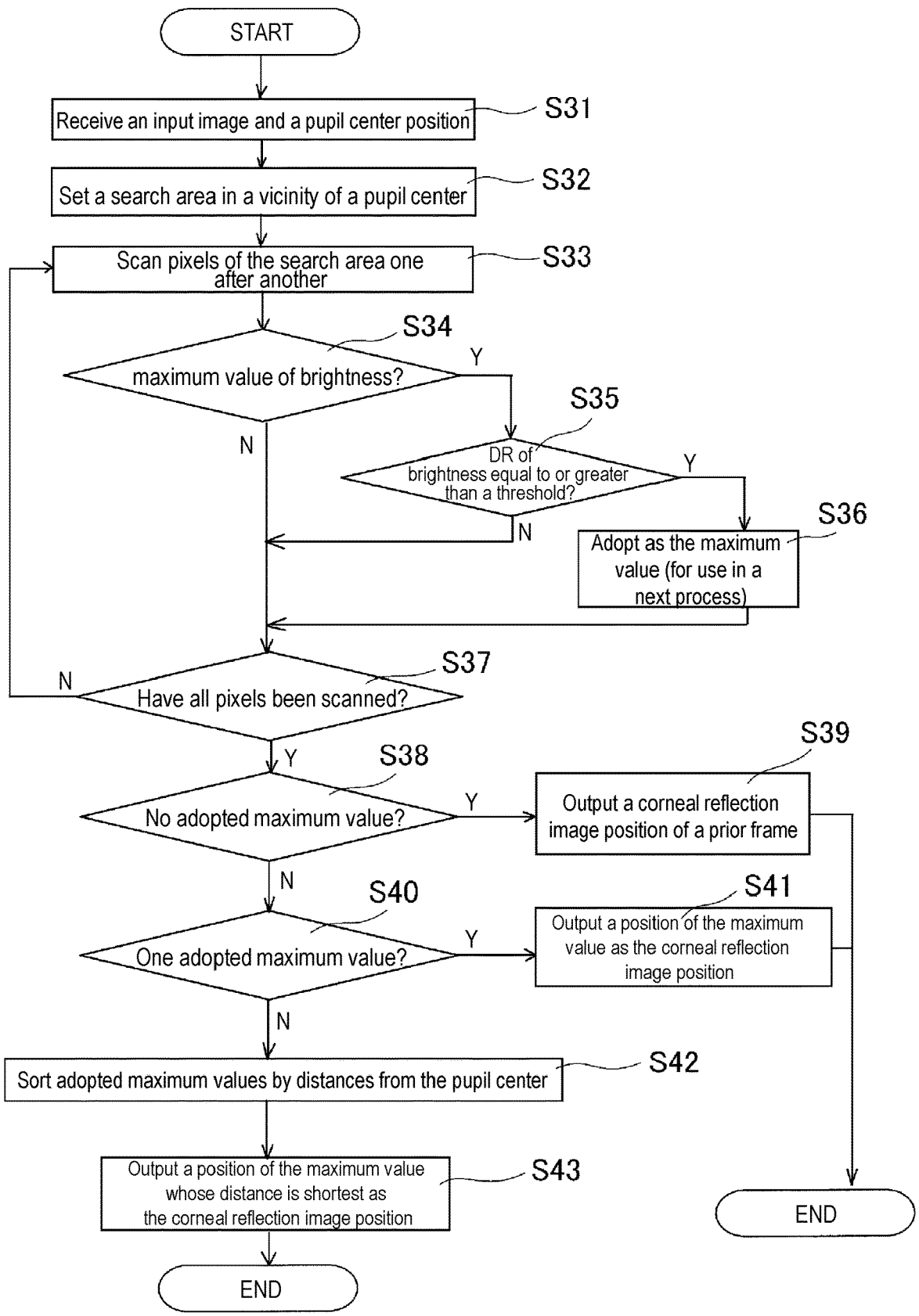
FIG. 12 is a flowchart illustrating detection processing operations for a corneal reflection image position performed by a gaze detection processing unit in a gaze detector according to an embodiment.

Since the situations shown in FIGS. 11a to 11c are possible, the detection of the position of the corneal reflection image is configured as the detection based on the flowchart shown in FIG. 12.

FIG. 12 is a flowchart illustrating detection processing operations for the corneal reflection image position performed by the gaze detection processing unit.

Firstly, in Step S31, a coordinate value of the pupil center and the imaged image when the projector unit is turned on are received. Then, in Step S32, a search area in the vicinity of the pupil center is set. Then, in Step S33, pixels of the search area are scanned one after another. Here, the expression "scan" refers to decomposing the image into a plurality of points, converting the brightness/darkness, etc., of the respective points into electrical signals, and searching through the respective points in a fixed order.

Then, in Step S34, whether the maximum value that is adoptable in the brightness distribution is reached is determined. If it is determined that the maximum value that is adoptable in the brightness distribution is reached in Step S34, Step S35 is performed. In Step S35, whether a dynamic range DR of brightness becomes equal to or greater than a threshold is determined. If it is determined that the dynamic range DR of brightness becomes equal to or greater than the threshold, Step S36 is performed, and a process for adopting the brightness value as the maximum value is performed. Regarding the dynamic range DR, the difference between the maximum value and the minimum value of brightness is adopted.

Alternatively, if it is determined in Step S34 that the maximum value that is adoptable in the brightness distribution is not reached, Step S37 is then performed. In Step S37, whether all the pixels have been scanned is determined.

In addition, in the case in which it is determined that the dynamic range DR of brightness is not equal to or greater than the threshold in Step S35, after performing the process for adopting the value of the brightness as the maximum value in Step S36, Step S37 is also performed.

If it is determined in Step S37 that not all the pixels have been scanned, the flow returns to Step S33. Alternatively, if it is determined in Step S37 that all the pixels have been scanned, Step S38 is then performed.

Then, in Step S38, whether there is no maximum value that is adoptable in the brightness distribution is determined. If it is determined in Step S38 that there is no maximum value that is adoptable in the brightness distribution, Step S39 is performed, and the corneal reflection image position of the prior frame is output.

If it is determined in Step S38 that there is a maximum value that is adoptable in the brightness distribution, Step S40 is then performed. In Step S40, whether there is one maximum value that is adoptable in the brightness distribution is determined. If it is determined in Step S40 that there is one maximum value that is adoptable in the brightness distribution, Step S41 is then performed. In Step S41, the position of the maximum value is output as the corneal reflection image position.

Alternatively, if it is determined in Step S40 that the maximum value that is adoptable in the brightness distribution is not one, Step S42 is then performed, and a process for sorting the maximum values that are adoptable by the distances from the pupil center is performed. Then, in Step S43, a process for outputting the maximum value with the shortest distance from the pupil center as the corneal reflection image position is performed.

By performing the above processes, the detection of the corneal reflection image position can be accurately performed.

The above processes from Step S31 to Step S43 serve to describe in detail the contents of the detection process for the corneal reflection image position in Step S24 for the gaze detection process shown in FIG. 6.

While the calculation method of the eye three-dimensional position vector is not recited in detail herein, a method for calculating a detailed three-dimensional position vector by using pattern light has been described in detail in Japanese Patent Application No. 2016-202682 previously filed by the applicant. For example, the method set forth in the specification of the aforementioned application may be adopted.

If, by measuring the detailed three-dimensional position vector using pattern light, the correct distance from the camera unit 10, 10A to the eye can be obtained, a three-dimensional dot group of the face surface can be obtained, and a face surface model is fit to the dot group, the orientation of the face can be obtained.

Since the calculation of the gaze by using the pupil center and the corneal reflection image is to calculate the deviation of the gaze from the orientation direction of the face, if the orientation of the face is accurately obtained by measuring the three-dimensional position vector, the gaze direction is also accurately obtained.

In addition, if the fitting is performed for each frame, the change of the orientation of the face over time can be calculated, and consequently the head movement can also be accurately calculated.

In addition, if the change of the pupil over time is detected with the imaged images of the camera unit 10, 10A, the eye movement can be accurately obtained.

Meanwhile, VOR induced by the head movement is an involuntary eye movement which reverses the eyeball at a substantially same speed during the head movement and suppresses blurring of the retinal image.

With the gaze detector 1 according to the embodiment, as described above, the head movement can be accurately calculated, and the eye movement can also be accurately obtained. Therefore, the gaze detector 1 is also capable of serving as a VOR measurement apparatus.

In addition, since the gaze detector 1 according to the embodiment can accurately detect the three-dimensional shape of the face surface of a person, the gaze detector 1 can carry out face recognition can by grasping the shape features of the face, and is also capable of serving as a person face recognition apparatus.

As a gaze calculation method, for example, descriptions have been made in detail in "Ohno Takehiko, et. al., 'Just Look at Two Points: A Gaze Tracking System with Easy Calibration', Transactions of Information Processing Society of Japan, Vol. 44, No. 4, pp. 1136-1149 (2003)", and the method described in this journal article may also be adopted. However, the gaze calculation method of the invention is not limited to the method described in this journal article, and other methods may also be suitable.

Also, regarding the details of VOR measurement, descriptions have been made in detail in "Nishiyama Junpei, et. al., 'Prediction of Drowsiness by the Vestibulo-Ocular Reflex', Transactions of Japanese Society for Medical and Biological Engineering, Vol. 48, No. 1, pp. 1-10 (2010, February)", and the method described in this journal article can be adopted. However, the VOR measurement method of the invention is not limited to the method described in this journal article, and other methods may also be suitable.

Although the embodiments of the invention have been described above in detail, the above description is merely examples of the invention in all respects. It goes without saying that various improvements and changes can be made without departing from the scope of the invention.

While the gaze detector mounted in a driver monitoring system and used for gaze measurement is described as an example in the above embodiment, the gaze detector may also be a gaze detector disposed in a work site such as a factory and used for gaze measurement in other embodiments.

In addition, in the above embodiment, the difference between the maximum value and the minimum value of brightness is adopted in the dynamic range in Step S35. However, in other embodiments, the difference between the maximum value and the median value of brightness may also be adopted as the dynamic range DR. With such setting, the detection of the corneal reflection image position used for gaze detection can be more resistant to noise.

In addition, in the above embodiment, if it is determined in Step S38 that there is no maximum value that is adoptable in the brightness distribution, the process for outputting the corneal reflection image position of the prior frame is performed in Step S39. However, in other embodiments, if it is determined in Step S38 that there is no maximum value adoptable in the brightness distribution, the current corneal reflection image position predicted from a prior frame, such as several prior frames, may also be output in Step S39. With such process, even in the case where a person is moving, the output of the corneal reflection image position used for gaze detection can be performed more properly.

APPENDIX

Embodiments of the invention may be described as the following of the appendix. However, the embodiments of the invention are not limited thereto.

Appendix 1

A method for controlling a gaze detector (1) includes: a step (S1) of turning on the projection unit and projecting the pattern light to the face of the person; a step (S2) of imaging the face on which the pattern light is projected by the camera unit; a step (S3) of outputting an image imaged in the step (S2) to the gaze detection processing unit; a step (S4) of turning off the projection unit; a step (S5) of imaging face on which the pattern light is not projected by the camera unit; and a step (S6) of outputting an image imaged in the step (S5) to the gaze detection processing unit.

Appendix 2

A method for detecting a corneal reflection image position is a method for detecting the corneal reflection image position for gaze detection using any one of the gaze detector (1) to (6). The method includes: a step (S31) of receiving the imaged image and a pupil center position; a step (S32) of setting a search area in a vicinity of the pupil center position; a step (S33) of scanning pixels in the search area one after another; a step (S34) of determining whether a scanning result becomes a maximum value of brightness; a step (S36) of adopting a value of the brightness as the maximum value if it is determined that a dynamic range of brightness is equal to or greater than a threshold; and a step (S43) of outputting a position of a pixel which denotes the maximum value and has a shortest distance from the pupil center as the corneal reflection image position.

Appendix 3

A computer program is a computer program for causing at least one computer to execute a detection process for a position of a corneal reflection image for gaze detection using the gaze detector (1). The computer program causes the at least one computer to execute: a step (S31) of receiving the imaged image and a pupil center position; a step (S32) of setting a search area in a vicinity of the pupil center position; a step (S33) of scanning pixels in the search area one after another; a step (S34) of determining whether a scanning result becomes a maximum value of brightness; a step (S36) of adopting a value of the brightness as the maximum value if it is determined (S35) that a dynamic range of brightness is equal to or greater than a threshold; and a step (S43) of outputting a position of a pixel which denotes the maximum value and has a shortest distance from the pupil center as the corneal reflection image position.

INDUSTRIAL AVAILABILITY

The invention is applicable for various systems that monitor people, such as a driver monitoring system for monitoring an driver of a vehicle, or a system disposed in a work site, etc., and measuring the gaze of an operator, etc., and can be widely used in various fields of industry.

What is claimed is:

1. A gaze detector, comprising:
a camera unit, imaging a face of a person;
a projection unit, projecting prescribed pattern light to the face of the person;
a control unit, controlling presence of projection of the pattern light by the camera unit and the projection unit; and
a gaze detection processing unit, detecting a gaze from an image of the face of the person imaged by the camera unit.

2. The gaze detector as claimed in claim 1, wherein: the gaze detection processing unit comprises:
a first calculation unit, using an image of the face which is imaged by the camera unit and in which the pattern light is not projected to calculate a pupil center in an eye of the person;
a second calculation unit, using an image of the face which is imaged by the camera unit and in which the pattern light is projected to calculate a position of a corneal reflection image in the eye of the person; and
a third calculation unit, using the image of the face which is imaged by the camera unit and in which the pattern light is projected to calculate a three-dimensional position vector of a predetermined part of the face.

3. The gaze detector as claimed in claim 1, comprising:
a fourth calculation unit, detecting a change of a pupil center in an eye of the person over time to calculate an eye movement;
a fifth calculation unit, detecting a surface shape of the face from a three-dimensional position vector of a predetermined part of the face and calculating a head movement of the person based on a change of an orientation of the surface shape over time,
wherein the gaze detector uses the eye movement and the head movement to detect vestibulo-ocular reflex (VOR).

4. The gaze detector as claimed in claim 1, comprising:
a sixth calculation unit, calculating a surface shape of the face of the person from a three-dimensional position vector of a predetermined part of the face of the person,
wherein the gaze detector uses the calculated surface shape of the face of the person to perform face recognition.

5. The gaze detector as claimed in claim 1, wherein a prescribed pattern of the pattern light becomes a binary pattern that differs for each location.

6. The gaze detector as claimed in claim 1, wherein the projection unit projects the pattern light with light in a predetermined invisible wavelength range,
the camera unit is sensitive in the predetermined wavelength range, and
the gaze detector further comprises an illuminator that emits the light in the predetermined wavelength range.

7. A method for controlling the gaze detector as claimed in claim 6, the method comprising:
a step of turning on the projection unit and turning off an illuminator;
a step of imaging the face on which the pattern light is projected by the camera unit;
a step of outputting an image imaged in the step to the gaze detection processing unit;
a step of turning off the projection unit and turning on the illuminator;
a step of imaging the face on which the pattern light is not projected by the camera unit; and
a step of outputting an image imaged in the step to the gaze detection processing unit.

8. A method for controlling the gaze detector as claimed in claim 1, the method comprising:
a step of turning on the projection unit and projecting the pattern light to the face of the person;
a step of imaging the face on which the pattern light is projected by the camera unit;

a step of outputting an image imaged in the step to the gaze detection processing unit;
a step of turning off the projection unit;
a step of imaging the face on which the pattern light is not projected by the camera unit; and
a step of outputting an image imaged in the step to the gaze detection processing unit.

9. A method for detecting a corneal reflection image position, which is a method for detecting the corneal reflection image position for gaze detection using the gaze detector as claimed in claim 1, the method comprising:
a step of receiving the imaged image and a pupil center position;
a step of setting a search area in a vicinity of the pupil center position;
a step of scanning pixels in the search area one after another;
a step of determining whether a scanning result becomes a maximum value of brightness;
a step of adopting a value of the brightness as the maximum value if it is determined that a dynamic range of brightness is equal to or greater than a threshold; and
a step of outputting a position of a pixel which denotes the maximum value and has a shortest distance from the pupil center as the corneal reflection image position.

10. The method for detecting the corneal reflection image position as claimed in claim 9, wherein a difference between the maximum value and a minimum value of brightness is set as the dynamic range.

11. The method for detecting the corneal reflection image position as claimed in claim 9, wherein a difference between the maximum value and a median value of brightness is set as the dynamic range.

12. The method for detecting the corneal reflection image position as claimed in claim 9, comprising:
a step of outputting, in a case where it is determined that there is no maximum value that is adoptable in a brightness distribution, the corneal reflection image position of a prior frame.

13. The method for detecting the corneal reflection image position as claimed in claim 9, comprising:
a step of outputting, in a case where it is determined that there is no maximum value that is adoptable in a brightness distribution, a current corneal reflection image position predicted from a prior frame.

14. The method for detecting the corneal reflection image position as claimed in claim 9, comprising:
a step of outputting, in a case where it is determined that there is one maximum value that is adoptable in a brightness distribution, a position of the maximum value as the corneal reflection image position.

15. A computer readable recording medium, which is a computer readable recording medium storing a computer program for causing at least one computer to execute a detection process for a position of a corneal reflection image for gaze detection using the gaze detector as claimed in claim 1, wherein:
the computer readable recording medium stores the computer program that causes the at least one computer to execute:
a step of receiving the imaged image and a pupil center position;
a step of setting a search area in a vicinity of the pupil center position;
a step of scanning pixels in the search area one after another;
a step of determining whether a scanning result becomes a maximum value of brightness;
a step of adopting a value of the brightness as the maximum value if it is determined that a dynamic range of brightness is equal to or greater than a threshold; and
a step of outputting a position of a pixel which denotes the maximum value and has a shortest distance from the pupil center as the corneal reflection image position.

\* \* \* \* \*